US006755321B2

(12) United States Patent
Solovay et al.

(10) Patent No.: US 6,755,321 B2
(45) Date of Patent: Jun. 29, 2004

(54) DISPENSER FOR ADHESIVE-BACKED ARTICLES

(75) Inventors: Kenneth S. Solovay, Weston, FL (US); James H. Layer, Cooper City, FL (US); Gregory Madden, Fort Lauderdale, FL (US); Elizabeth Peacock, Weston, FL (US)

(73) Assignee: ASO Corporation, Sarasota, FL (US)

( * ) Notice: Subject to any disclaimer, the term of this patent is extended or adjusted under 35 U.S.C. 154(b) by 25 days.

(21) Appl. No.: 10/126,970

(22) Filed: Apr. 22, 2002

(65) Prior Publication Data

US 2002/0170918 A1 Nov. 21, 2002

Related U.S. Application Data

(60) Provisional application No. 60/285,237, filed on Apr. 23, 2001.

(51) Int. Cl.⁷ ................................................ B65H 5/28
(52) U.S. Cl. ............................. 221/73; 221/26; 221/71; 221/72
(58) Field of Search .................. 221/70, 71, 73, 221/25, 26

(56) References Cited

U.S. PATENT DOCUMENTS

| | | | |
|---|---|---|---|
| 1,809,523 A | | 6/1931 | McLean |
| 3,530,494 A | | 9/1970 | Baratta |
| 4,111,333 A | * | 9/1978 | Norgaard ..................... 221/73 |
| 4,265,234 A | | 5/1981 | Schaar |
| 4,570,868 A | * | 2/1986 | Wiggs et al. ............ 242/55.53 |
| 4,993,586 A | * | 2/1991 | Taulbee et al. ................ 221/25 |
| 5,065,894 A | * | 11/1991 | Garland ......................... 221/25 |
| 5,234,093 A | * | 8/1993 | Abe et al. .................... 194/296 |
| 5,261,563 A | * | 11/1993 | Brimhall ....................... 221/73 |
| 5,358,140 A | | 10/1994 | Pellegrino |
| 5,383,900 A | | 1/1995 | Krantz |
| 5,511,689 A | * | 4/1996 | Frank ............................ 221/73 |
| 5,806,714 A | * | 9/1998 | Geiger ........................ 221/73 |
| 6,124,522 A | | 9/2000 | Schroeder |
| 6,171,439 B1 | | 1/2001 | Groeneweg |
| 6,213,343 B1 | * | 4/2001 | Damikolas .................... 221/25 |
| 6,225,522 B1 | | 5/2001 | Schroeder |
| 6,299,018 B1 | * | 10/2001 | Kimbrell ....................... 221/71 |
| 6,431,397 B1 | * | 8/2002 | Fishman ....................... 221/73 |

FOREIGN PATENT DOCUMENTS

| | | |
|---|---|---|
| DE | 31 28 547 A | 2/1983 |
| WO | WO 95 18046 | 7/1995 |
| WO | WO 99 24341 | 5/1999 |

* cited by examiner

*Primary Examiner*—Donald P. Walsh
*Assistant Examiner*—Kaitlin Joerger
(74) *Attorney, Agent, or Firm*—Banner & Witcoff, Ltd.

(57) ABSTRACT

A dispenser that is mountable on a vertical or horizontal surface for dispensing adhesive-backed articles from a bulk stock using a single hand. The dispenser includes a housing having a bucket portion for receiving and containing the adhesive-backed articles to be dispensed and a cover connected to the bucket portion. The cover includes a window through which the adhesive-backed articles can be removed from the backing sheet and applied to a person or other animal using a single hand. The dispenser also includes a support member secured within the housing such that at least one of the cover and the support member is biased toward the other for preventing movement of the backing sheet as one of the adhesive-backed articles is removed from the backing sheet through the window.

30 Claims, 14 Drawing Sheets

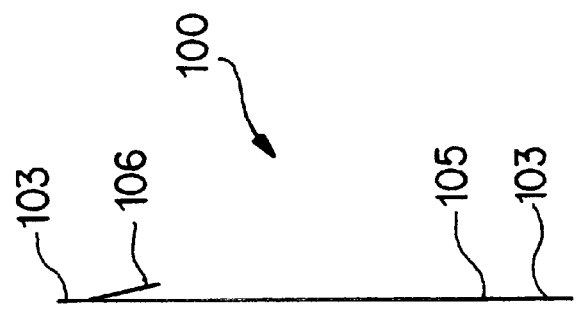
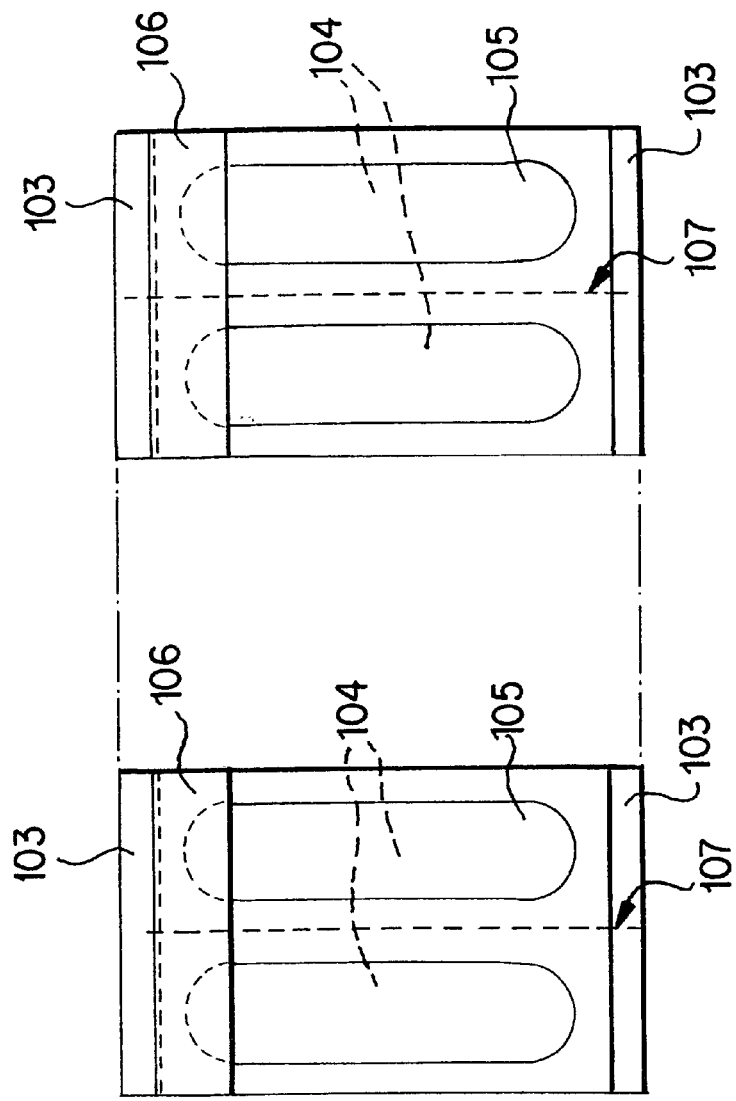

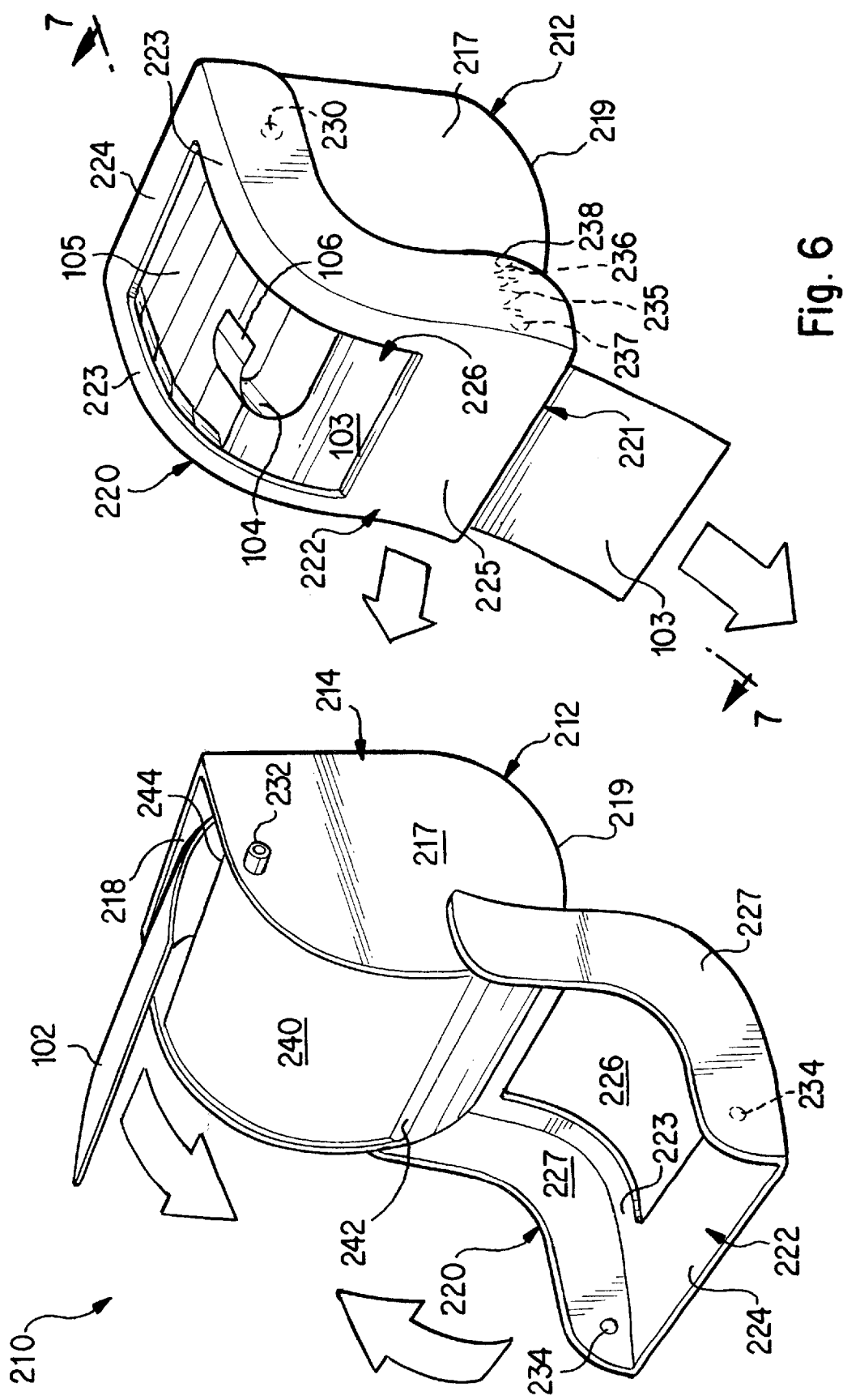

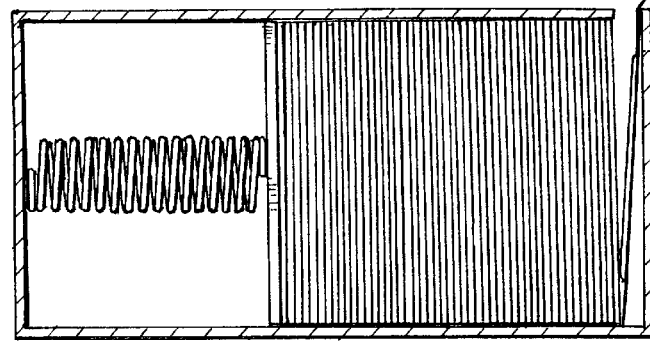
Fig. 9
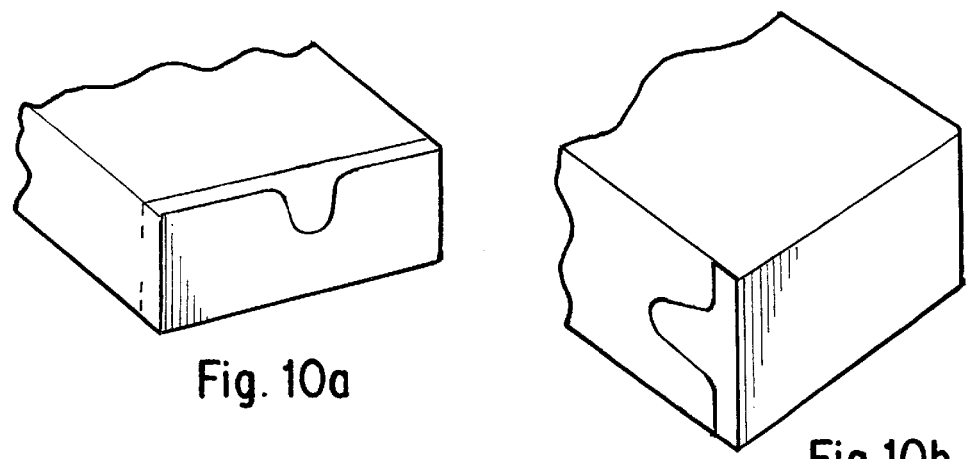
Fig. 10a
Fig. 10b
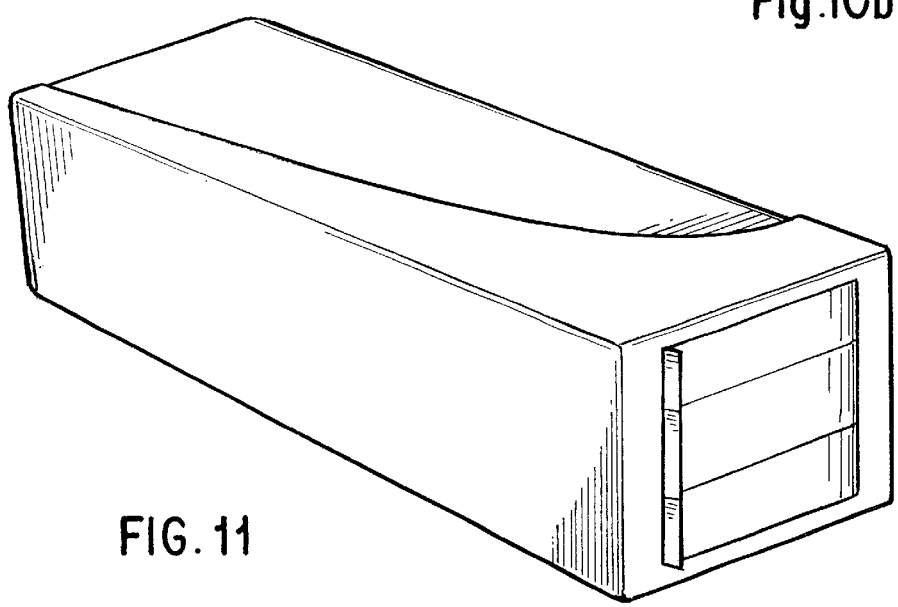
FIG. 11

DISPENSER FOR ADHESIVE-BACKED ARTICLES

Benefit of the Apr. 23, 2001 filing date of U.S. Provisional Application Serial No. 60/285,237 by the same inventors and entitled "Dispenser For Adhesive-Backed Articles" is hereby claimed.

The present invention relates to a dispenser for adhesive-backed articles, more particularly, it relates to a dispenser for adhesive-backed articles, such as bandages, that can be applied using a single hand.

BACKGROUND OF THE INVENTION

Adhesive-backed articles such as adhesive bandages are known in the art. These bandages are commonly sealed in sterile wrappings and packaged either on a continuous roll or within paper or metal boxes. Examples include the well-known Band-Aid® brand bandages. While popular, these products suffer certain disadvantages such as the fact that the bandages themselves can be difficult to remove from their individual wrappings and difficult to apply to the desired location. The user generally must remove the bandage from the wrapping, remove nonstick cover layers from the adhesive portions of the bandage and then attempt to apply the bandage to the desired location while compromising the sterility of the bandage or having the bandage curling and adhering to itself or the person applying the bandage. These traditional bandages are not designed so they can be removed from their packaging and applied to a patient using only a single hand.

U.S. Pat. No. 5,511,689 to Frank and U.S. Pat. No. 6,124,522 to Schroeder, which are both hereby expressly incorporated by reference, both disclose bandages that are packaged so they can be removed from a backing strip, applied to a patient and separated from their cover using only a single hand. The packaging for these bandages can include separate, individually sealed packages or a plurality of sealed packages that share a common, elongated backing sheet.

Dispensers for bandages that share a common, elongates backing sheet are known. Typically, the backing sheet assumes the form of a roll that is positioned within the dispenser so that it can rotate or otherwise move relative to the housing of the dispenser. U.S. Pat. No. 4,993,586 to Taulbee, et al. discloses a known bandage dispenser in which a continuous strip is grasped with one hand and a bandage is removed with the other hand. This is accomplished using a continuous backing strip with first and second layer. Bandages are placed on sterile mounting pads affixed to the first layer. The bandages and the first layer are then enclosed by a cover layer and stacked or rolled within a container. In use, the sheet is pulled through a splicer attached to the container that cuts the first and second layer. The second layer is then lifted and removed. The first layer is then grasped with one hand and a bandage is removed with the other. Like other known dispensers, the dispenser disclosed in the patent to Taulbee et al. requires that the person removing the bandage and applying it use two hands. This can be impractical for a busy health care professional and impossible for a person who has injured one of their hands. Additionally, it can be very difficult and inconvenient for physically challenged people, such as amputees, to use a conventional, two-handed dispenser.

SUMMARY OF THE INVENTION

In view of the foregoing, it is useful to provide a dispenser for adhesive-backed articles that permit an adhesive based article to be taken from the dispenser with one hand. In particular, when using adhesive-backed articles (such as adhesive bandages, as discussed above) that can be applied to a location (such as a wound) with one hand, it is useful to provide a dispenser that permits such articles to be taken from the dispenser with one hand. Otherwise, a dispenser that requires a user to manipulate such an adhesive-backed article with both hands diminishes some of the utility of the articles and can cause the sterile portion of the bandage to be compromised.

In general, the present invention provides a dispenser for dispensing adhesive-backed articles from a bulk stock. Generally, bulk stock refers to a continuous web of backing material on which individual adhesive-backed articles are affixed and covered. The dispensers according to the present invention can be mounted to a wall, a horizontal surface or any other convenient location that permits a person to access the dispenser and remove one of a plurality of the adhesive-backed articles using a single hand.

In one embodiment, the dispenser includes a housing having a bucket portion for receiving and containing the bulk stock adhesive-backed articles to be dispensed and a cover connected to the bucket portion. The cover includes a window through which the adhesive-backed articles can be removed from the backing sheet and applied to a person or other animal using a single hand. The dispenser also includes a support member secured within the housing such that at least one of the cover and the support member is biased toward the other for preventing movement of the backing sheet as one of the adhesive-backed articles is removed from the backing sheet through the window. This prevents the need for someone to hold the backing sheet as the adhesive-backed article is removed.

In another embodiment of the present invention, the dispenser includes a feed roller and a pressure roller that cooperate to form a nip for receiving a section of bulk stock roll and advancing it within the dispenser. The received section of the bulk stock roll can include the backing material, the adhesive-backed article and any cover applied over the article. Alternatively, this section can include only the backing material. The dispenser also includes an activation mechanism that causes the rollers to rotate when it is operated. Rotating or otherwise moving a handle relative to a housing of the dispenser can cause the activation mechanism to operate and the rollers to rotate within the housing.

BRIEF DESCRIPTION OF THE FIGURES

FIG. 1b is a side elevational view of one the bandages on the common, continuous backing sheet illustrated in FIG. 1a;

FIG. 1d is a plan view of a portion of an alternative roll of adhesive-backed articles that can be used with the dispenser according to the present invention;

FIG. 1e is a side view of the portion of the alternative roll of the adhesive-backed articles shown in FIG. 1d;

FIG. 5 is a perspective view of the dispenser of FIG. 4 with a roll of bandages installed within the dispenser;

FIG. 6 is a perspective view of the dispenser of FIG. 4 with a cover in a closed position and the bandages being removed;

FIG. 9 is a cross-sectional view of an adhesive bandage dispenser according to the present invention;

FIG. 10a is a partial perspective view of an adhesive bandage dispenser according to an embodiment of the present invention;

FIG. 10b is a partial perspective view of an adhesive bandage dispenser according to another embodiment of the present invention;

FIG. 11 is a perspective view of an adhesive bandage dispenser according to another embodiment of the present invention;

DETAILED DESCRIPTION OF THE FIGURES

Figure 1A:
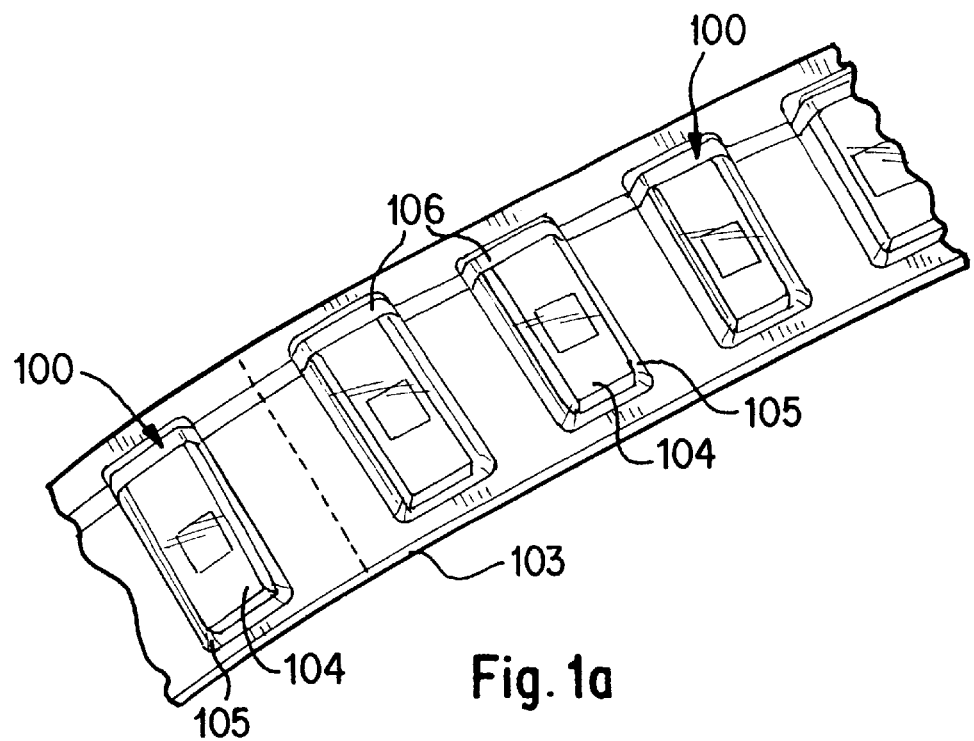
FIG. 1a is a perspective view of adhesive-backed articles positioned on a common backing sheet according to the present invention.

FIG. 1 illustrates adhesive-backed articles 100 that can be used with the below disclosed dispensers. These articles 100 can include bandages that are customarily applied to a patient to cover a wound or apply a medicament or other agent the body of the patient for therapeutic purposes as discussed in U.S. Pat. Nos. 6,124,522 and 6,225,522 to Schroeder that are hereby incorporated by reference.

The dispensers disclosed herein below can deliver any known type of individually packaged bandage. Also, they can dispense any known type of bandage that is carried on an elongated, continuous bulk backing sheet as disclosed in U.S. Pat. No. 5,511,689 to Frank that is hereby incorporated by reference. The continuous backing sheet can include transverse lines of perforations 107 between adjacent bandages. As shown in the figures, the bandages 104 and the elongated backing sheet 103 are wound into a continuous roll 102. Alternatively, the bandages could be folded on top of each other in a fan or "Z" form.

The embodiments of the dispenser herein will be described with respect to their dispensing bandages that are carried on the elongated, continuous bulk backing sheet 103. While other bulk bandages may be designed to fit in the dispenser, for clarity of explanation, the discussion of the bandages will be limited to those bandages that can be removed from the backing sheet 103 and applied to a patient using only a single hand. Examples of these bandages 104 that can be applied using a single hand include those disclosed in U.S. Pat. No. 5,511,689 to Frank, U.S. Pat. Nos. 6,124,522 and 6,225,522 to Schroeder and those commercially available under the mark QWIK-STRIP®. Hence, a complete discussion of these bandages will not be included.

As shown in FIGS. 1a–1e, the bulk roll 102 includes a backing sheet 103 and a plurality of adhesively backed bandages 104 that are shorter (narrower) than the backing sheet 103 in the direction that extends between the longitudinal side edges of the roll 102 that are parallel to the path of travel of the backing sheet 103. In a preferred embodiment the bandages 104 are at least one centimeter shorter than the backing sheet 103. As shown, the bandages 104 are placed on the backing sheet 103 in series and side-by-side. The bandages 104 can also extend parallel to the path of travel of the backing sheet 103.

Figure 1B:
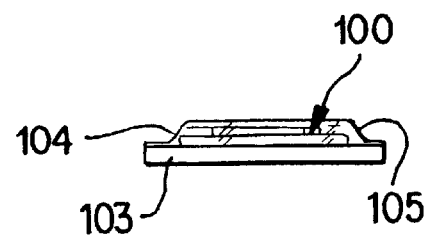
Figure 1C:
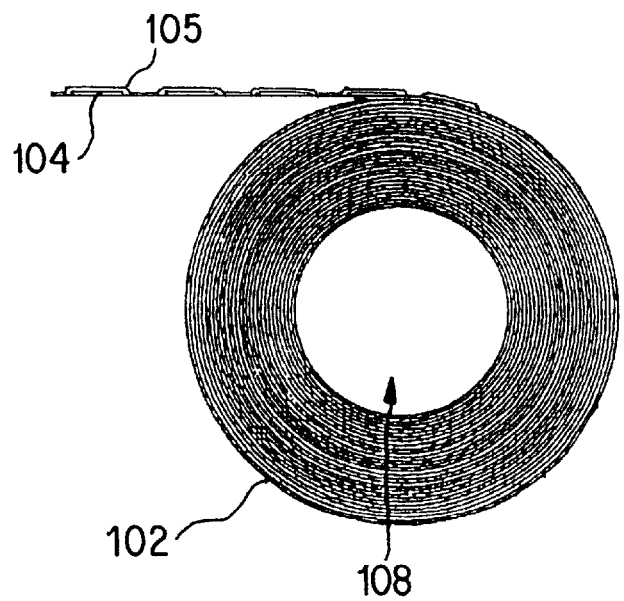
FIG. 1c is a side elevational view of a roll of adhesive-backed articles usable with the dispensers according to the present invention.

Each bandage 104 is covered by a separate, individual cover sheet 105 with a pull-tab 106 that forms a sterile enclosure around a bandage 104 with the backing sheet 103. As seen in FIGS. 1a and 1e, the ends of the cover sheets and the pull-tabs 106 are spaced from a longitudinal side edge of the backing sheet 103 by a distance sufficient to allow the pull tabs 106 to be exposed in a dispenser window for the reasons as discussed below, in a preferred embodiment this distance is about 0.25 inches. The ends of the cover sheets 105 and the pull-tabs 106 can be spaced a greater or lesser distance from the longitudinal side edges of the backing sheet 103 to accommodate the size of a dispenser window or to provide more contact between the dispenser and the backing sheet 103 during the removal of the bandages 104. Additionally, a transversely extending line of perforations 107 extends between adjacent cover sheets 105 so that the adjacent cover sheets can be easily separated from each other during the removal of a bandage 104 from the backing sheet 103. Alternatively, separate, discrete, individual coversheets 105 may be used to eliminate the need for perforations.

The sterile bandage enclosures are formed over the bandages 104 in the same way as disclosed in U.S. Pat. Nos. 6,124,522 and 6,225,522 to Schroeder. As a result of this arrangement, the bandages 104 and their cover sheets 105 can be removed from the backing sheet 103 as described in the Schroeder patents. Similarly, the bandages 104 can be applied to patients and then separated from their cover sheets using a single hand in the same manner as described in the Schroeder patent. Each roll 102 can carry between 500 and 1,400 bandages. In one embodiment, the roll 102 carries between 500 and 1,200 bandages.

The roll 102 can be wound around a shaft that is then loaded into one or more of the below discussed dispenser housings and received in bearing surfaces within the interior of the housing(s). Alternatively, a shaft that forms a permanent portion of one of the below discussed dispensers can be advanced through a hollow open core 108 of the roll 102 and then secured in place in the respective housing. The roll 102 may also be rotatably supported within the housing(s) by a pair of arms that are secured within the housing(s) and received within the open core of the hub. Alternatively, the roll 102 may also rest unsupported in the bucket. Other known mounting arrangements could also be used. In any of these embodiments using a roll 102 of bandages 104, the roll 102 rotates relative to the dispenser housing when the backing sheet 103 is advanced as discussed below.

Figure 2A:
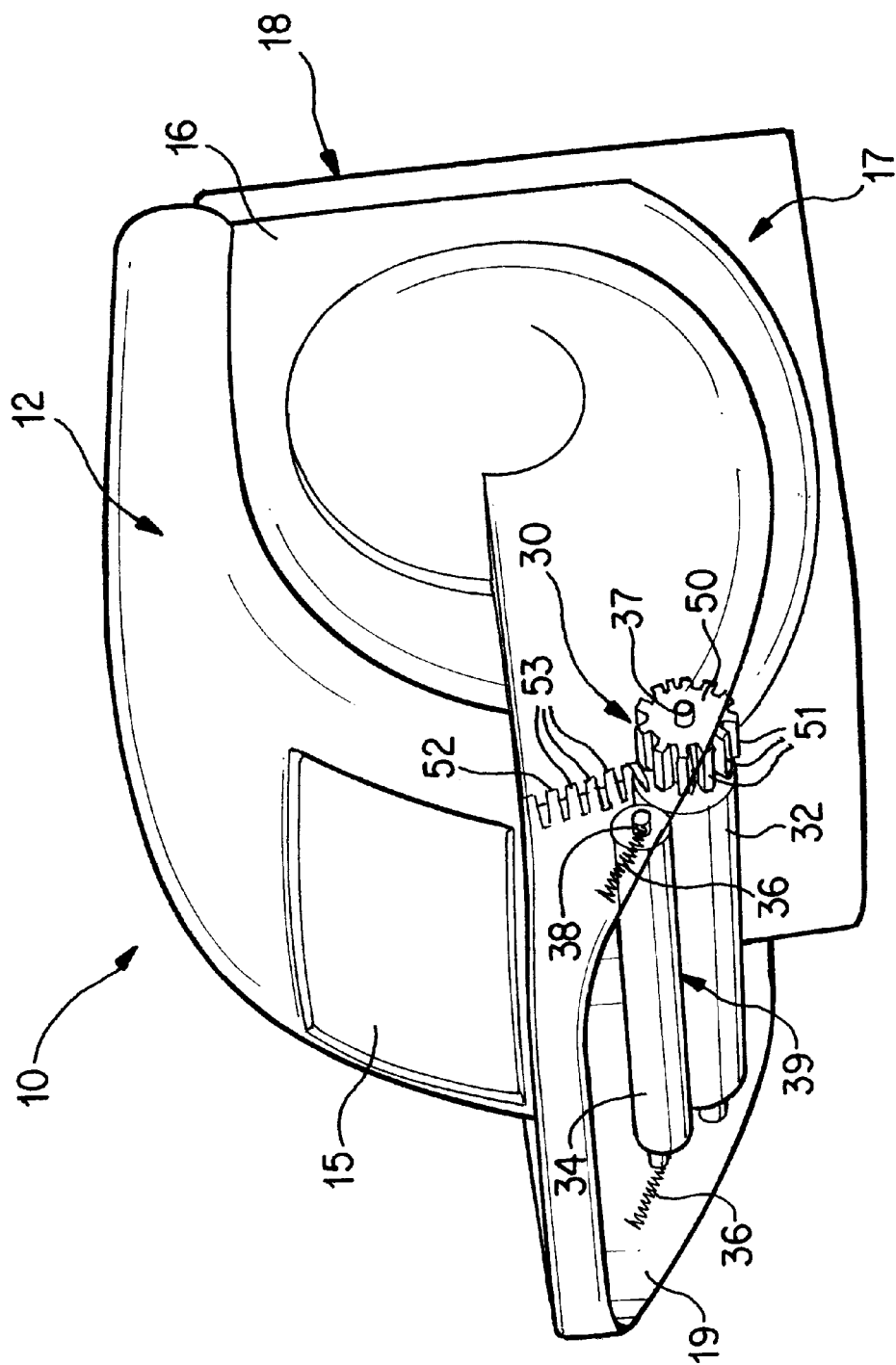
FIGS. 2a–2c are perspective views of a dispenser according to the present invention with FIG. 2c illustrating the interior of the dispenser.
Figure 2B:
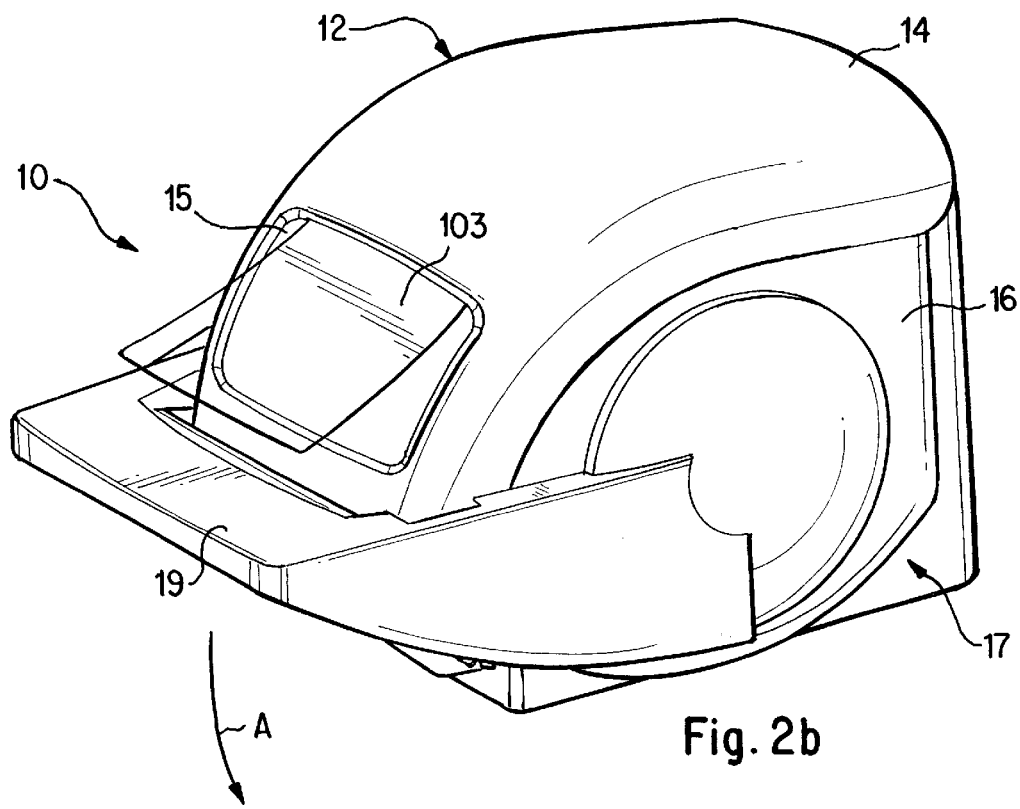
Figure 2C:
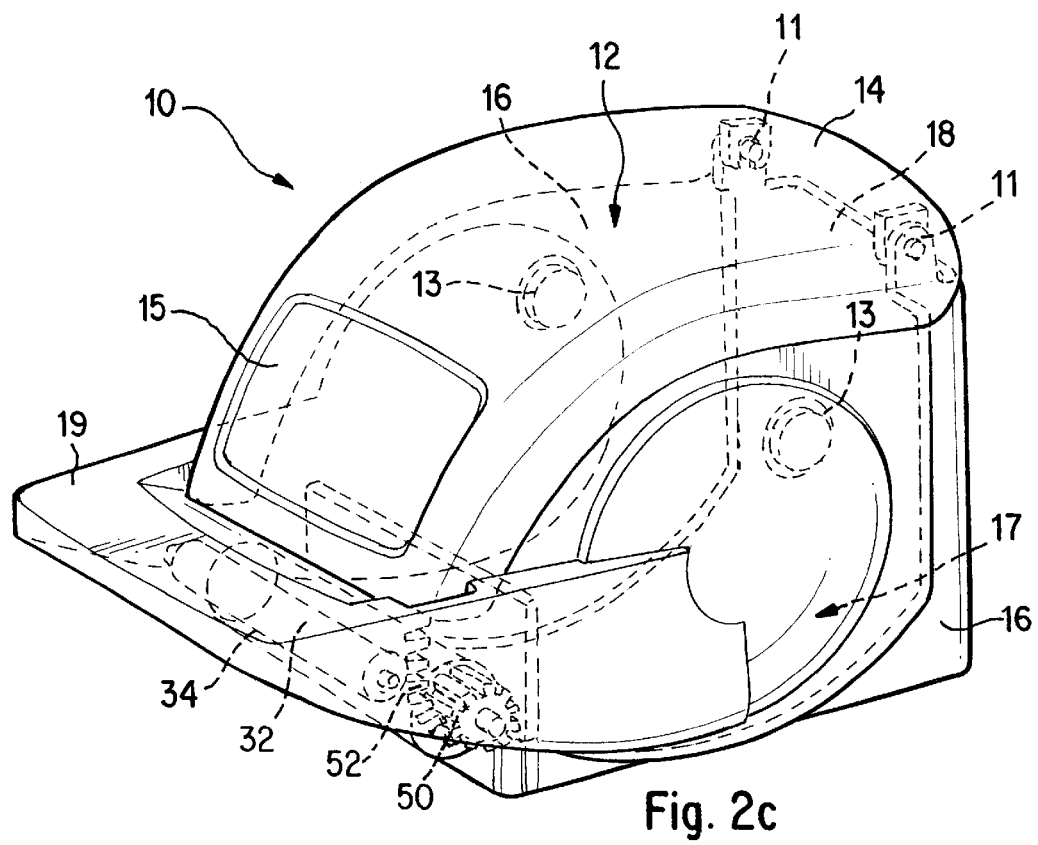
Figure 2E:
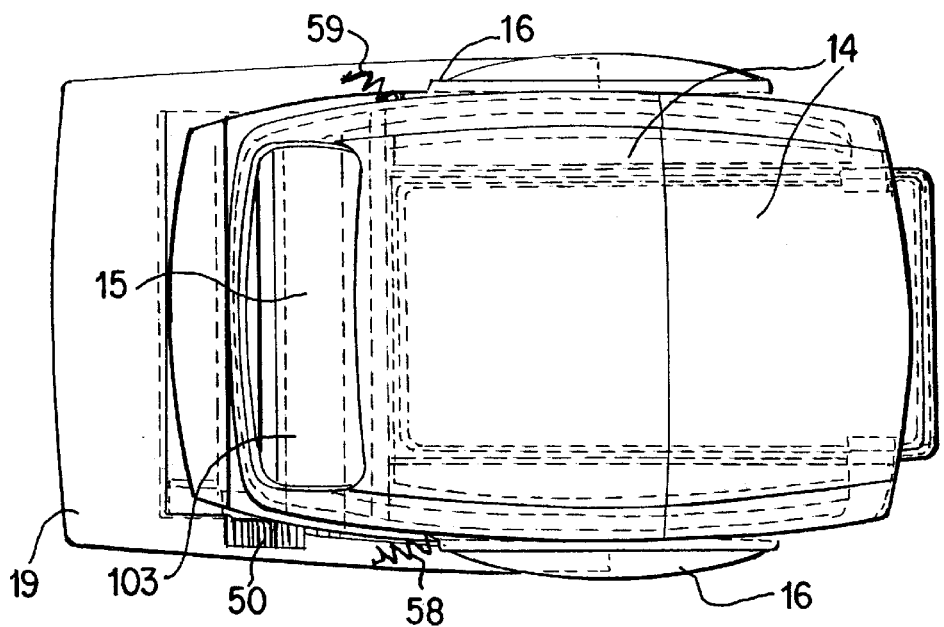
FIG. 2e is a top view of the dispenser illustrated in FIG. 2c.

As shown in FIGS. 2a–2c, a dispenser 10 includes a housing 12 with a front cover panel 14, opposing side panels 16 and a back panel 18. The opposing side panels 16 and the back panel 18 forming a bucket 17 for receiving the roll 102. The dispenser 10 also includes an operating handle 19 that can be connected to the side panels 16 by a rotatable pin 13 that extends into a bearing in the side panel 16. The front panel 14 includes an opening (window) 15 that permits bandages to be removed from the roll (reel) 102. The front panel 14 can be hinged or otherwise attached to the back panel 18 by a pin or a known pivoting hinge 11 so that the front panel 14 can be pivoted between an open position and a closed position. When the front panel 14 is in the open position, it is pivoted up and away from the side panels 16 to permit the loading of a roll 102 of bandages 100 in the housing 12. When pivoted to the closed position, the front panel 14 is received by or positioned in close proximity to the side panels 16 so that the loaded roll 102 of bandages 100 is enclosed within the dispenser 10 as shown in FIGS. 2a and 2b.

As shown in FIGS. 2a–2c, the dispenser 10 includes a bandage feeding system 30 mounted in the housing 12 for delivering the bandages 104 to the dispensing window 15 in the front panel 14. The feeding system 30 can be manually operated using the operating handle 19, as discussed below, or it can be operated using a known motor (not shown). The feeding system 30 includes a driven feed roller 32 and a pressure roller 34 that form a nip 39 for receiving a portion of the roll 102, advancing the roll 102 and delivering the bandages 104 to the window 15.

Figure 2D:
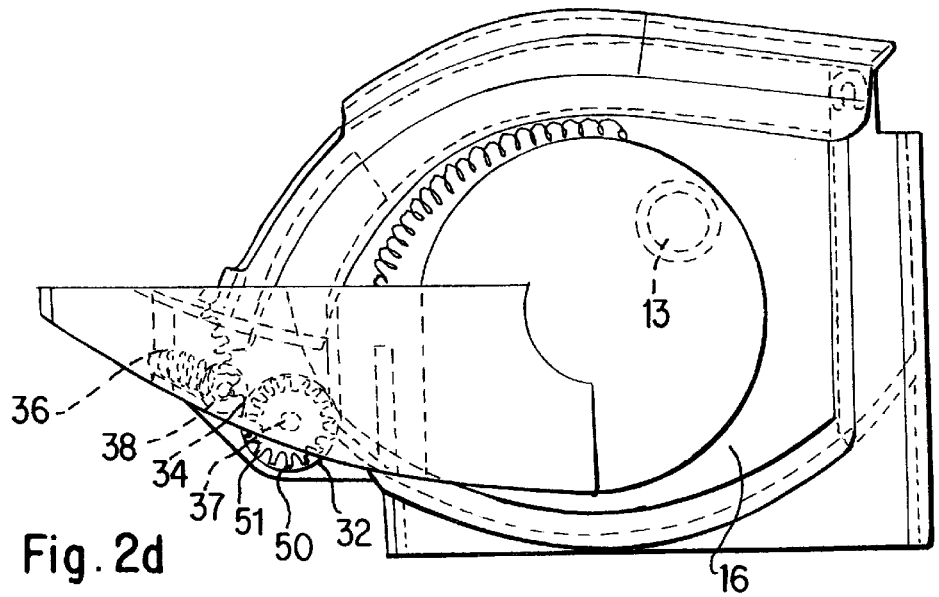
FIG. 2d is a side view of the dispenser illustrated in FIG. 2c.

As shown in FIG. 2a, axles 37, 38 mount the feed roller 32 and the pressure roller 34 within the housing 12, respectively. These axles 37, 38 are rotatably secured within the side panels 16. One end of the feed roller 32 includes a pinion 50 that is secured to the feed roller 32 so that the feed roller 32 and the pinion 50 rotate simultaneously in one direction and the feed roller 32 free wheels relative to the pinion 50 in the opposite direction. As shown in FIG. 2a, the teeth 51 of the pinion extend out from within the housing 12 for mating with rack 52 on an inside surface of the handle 19. Like the pinion 50, the rack 52 includes a plurality of teeth 53. When the handle 19 is pivoted in the direction of arrow "A" in FIG. 2b (advancing stroke), the teeth 53 engage the pinion 50 and cause it to rotate. The rotation of the pinion 50 in the direction of arrow A causes the feed roller 32 to rotate in the same direction as the pinion 50. As discussed below, the rotation of the feed roller 32 causes the bandages 104 to be advanced to the window 15. When the advancing stroke of the handle 19 has been completed, the handle 19 rotates back in a direction opposite direction A until it reaches its original rest position. As this occurs, the pinion 50 spins freely (free wheels) relative to the feed roller 32. In one embodiment, a spring 58 secured between the handle 19 and a portion of the housing 12, as shown in FIG. 2d, aids the return motion of the handle 19 to its original, rest position.

The position of the pressure roller 34 relative to the feed roller 32 can be securely maintained so that it is in constant contact with the feed roller 32. In another embodiment shown in FIG. 2a, the pressure roller 34 is biased in the direction of the feed roller 32 by at least one spring 36. The spring 36 allows the pressure roller 34 to move relative to the feed roller 32 and apply constant pressure against the feed roller 32 so that these two rollers 32, 34 rotate together and in opposite directions. Also, the spring loaded pressure roller 34 allows webs of different thickness to be received in the nip 39 and advanced as the pressure roller 34 and feed roller 32 are rotated in response to the advancing stroke of the handle 19. For example, the pressure roller 34 will apply pressure and cause the backing sheet 103 to be advanced in response to the operation of the feeding system 30 when only the backing sheet 103 is positioned in the nip 39. The pressure roller 34 will also apply pressure so that the backing sheet 103, bandage 104 and cover sheet 105 can all be advanced when they are positioned in the nip 39 without the dispenser 10 jamming. As can be readily understood, when only the backing sheet 103 is advanced through the nip 39, the bandages are advanced in the direction of the nip 39 within the housing 12 and to the window 15.

During the operation of the dispenser 10, the bandages 104 are delivered to the window 15 so that they can be removed from backing sheet 103 and applied to a patient. The rollers 32, 34 advance a portion of the roll 102 within the nip 39 so that at least one bandage 104 is delivered to the window 15 or a discharge opening 48 (shown in FIG. 3a) at a forward end when the dispenser 10 is operated. In one embodiment, only one bandage is delivered by each operation of the feeding mechanism 30. In another embodiment, multiple bandages 104 from the roll 102 are delivered with each operation of the feeding mechanism 30. In any of the above instances, the delivered bandage(s) can extend across the backing sheet transverse to the path of motion or they can extend parallel to the path of travel of the backing sheet 103. The portions of the backing sheet 103 that pass through the nip 39 can extend through the opening 48. When this occurs, the extended end of the roll 102 will be torn off at a random position or along a line of perforations and thrown away. Alternatively, the end of the roll 102 can be collected in a well in the housing 12 after it passes through the nip 39.

Figure 2F:
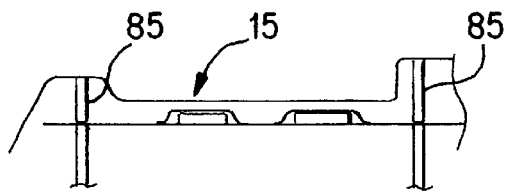
FIG. 2f is a partial cross section through a portion of the dispenser that illustrates holding members that apply pressure to a backing layer around bandages to prevent the backing layer from exiting the dispenser as a bandage is being taken from a bulk roll of bandages positioned within the dispenser.

As discussed above, and in greater detail in the Schroeder patents, the packaging of each bandage 104 permits it to be quickly and easily removed from the backing sheet 103 at the window 15, applied to the patient and separated from their cover sheet 105 using only a single hand. The dispenser 10 compliments the easy bandage removal discussed in the patents to Schroeder and Frank. The dispenser 10 includes a pair of substantially rigid protruding members 85 that cooperates with the interior portions of the dispenser 10 to support the backing sheet 103 as shown in FIG. 2f. The members 85 apply a holding pressure to areas of the backing sheet that are downstream from the bandages 104 or that surround the bandages 104 in order to hold the backing sheet 103 in place within the dispenser 10 as the bandages 104 are removed from the backing sheet 103. In an embodiment, the dispenser 10 includes only one member 85 for engaging with an interior surface of the dispenser 10 to hold the backing sheet 103 during bandage 104 removal.

In one embodiment, each holding member 85 for the backing sheet 103 includes a set of rails that hold and apply pressure to the edges of backing sheet 103 as it passes by the window 15. These rails receive and apply pressure to the longitudinal edges of the backing sheet 103. In another embodiment, the holding member 85 includes a frame that extends around the window 15 and away from an inner surface of the front panel 14 and into the interior of the dispenser 10. In this embodiment, the frame portion of the front panel 14 around the window 15 lightly squeezes the backing sheet 103 against the interior of the dispenser 10 and holds it in place as the bandage 104 is removed. Alternatively, the clearance between the interior structure of the front panel 14 and the interior structure of the dispenser 10 that carries and supports the backing sheet 103 is small enough that it applies a slight pinching pressure to the backing sheet 103 and prevents it from being removed from the dispenser as the bandage is being separated from the backing sheet 103. In another embodiment, the holding members include axles carrying O-rings or other types of rotatable pressure application members that can be positioned on the downstream side or the downstream and upstream sides of the window 15 for applying pressure to the backing sheet 103 supported within the dispenser 10 in order to hold the backing sheet 103 steady as the bandages 104 are removed. Any known way of holding or applying pressure to the edges, sides, surfaces or corners of the backing sheet 103 around the bandages 104 could be used.

In the dispenser 10 illustrated in FIG. 2a, the rollers 32, 34 hold the backing sheet 103 in tension as it passes through the nip 39. As a result, each bandage 104 can be removed from the tightly held backing sheet 104 without the backing sheet 103 exiting out of the dispenser 10 through the window 15. Alternatively, the bandage 104 can be advanced through the nip 39 to the discharge opening 48 at the front of the housing 12. In this instance, the two hands may be used to initially separate the cover sheet 105 from the roll of backing sheet 103. In another embodiment, a plate or lip at the opening 48 of the dispenser 10 will perform this initial separation function so that the bandage 104 can be taken and applied using only one hand.

Figure 3A:
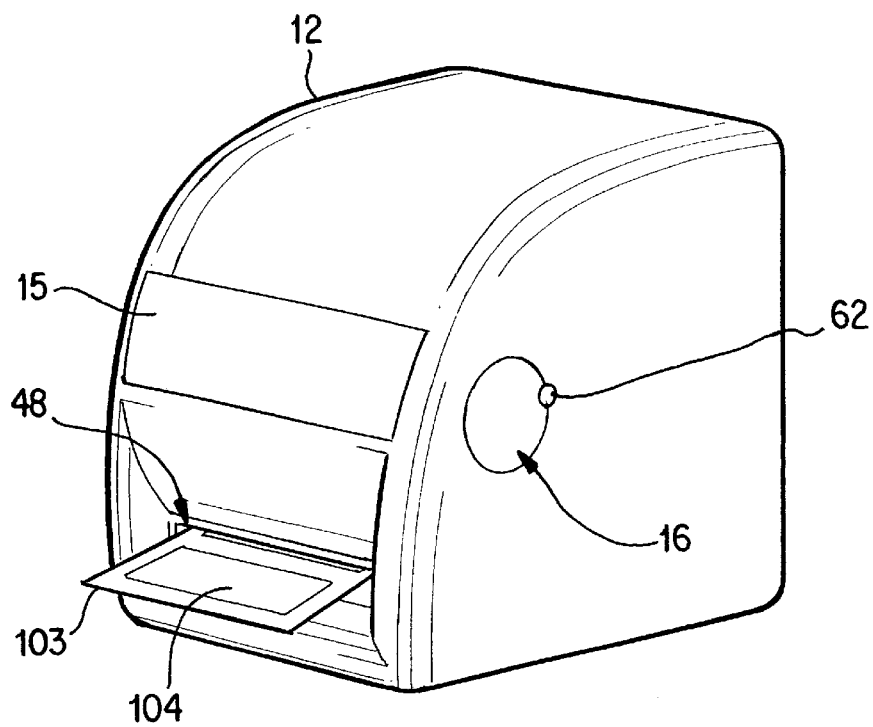
FIGS. 3a and 3b illustrate another embodiment of the dispenser that is similar to the dispenser disclosed in FIG. 1.
Figure 3B:
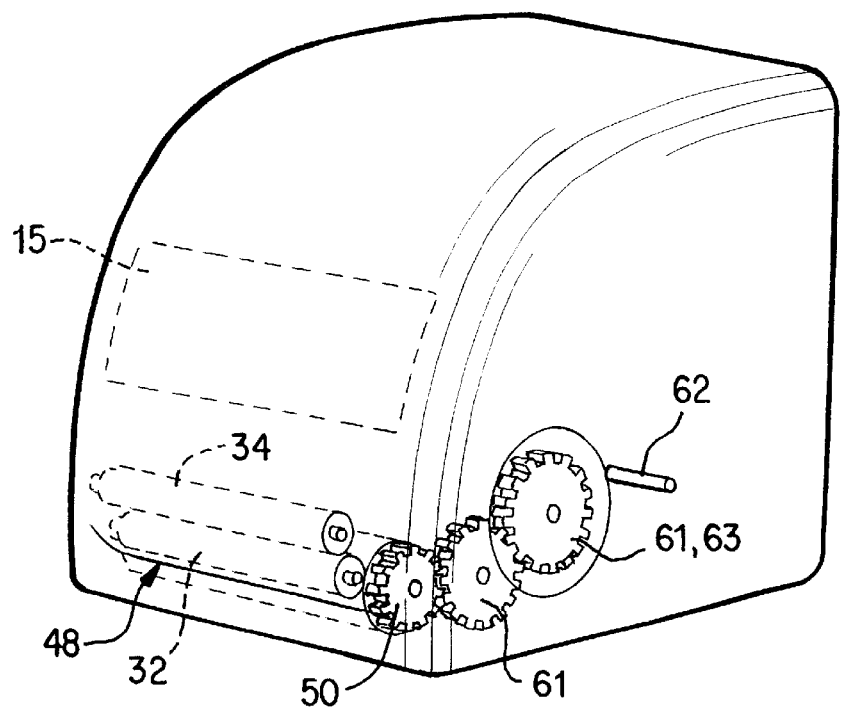

In another embodiment of the present invention illustrated in FIG. 3a, the dispenser is similar to that illustrated in FIG. 2a. However, a toothed gear 61 that is operatively connected to a crank handle 62 engages the pinion 50 and causes it to rotate. As a result, when the crank handle 62 is rotated in the direction of arrow A, the gear 61 meshes with the pinion 50 and the feed roller 32 is rotated so that the backing sheet 103 is advanced and the next bandage 104 is delivered to the window 15 or the discharge opening 48 as shown in FIG. 3b. The toothed gear 61 is operatively connected to the crank handle 62 by the gear 61 that rotates when the crank handle 62 is rotated. This can be accomplished by the gear 61 being directly secured to the crank handle 62 or by intermediate gears 63 that mesh with both the gear 61 and the crank handle 62 so that the gear 61, pinion 30 and rollers 32, 34 move in response to the rotation of the handle 62. As with the embodiment illustrated in FIG. 1, the bandages 104 can be removed from the backing sheet 103 at the window 15 because of the tension applied to the backing sheet 103 by the rollers 32, 34 holding the backing sheet 103 tight within the nip 39.

Figure 4:
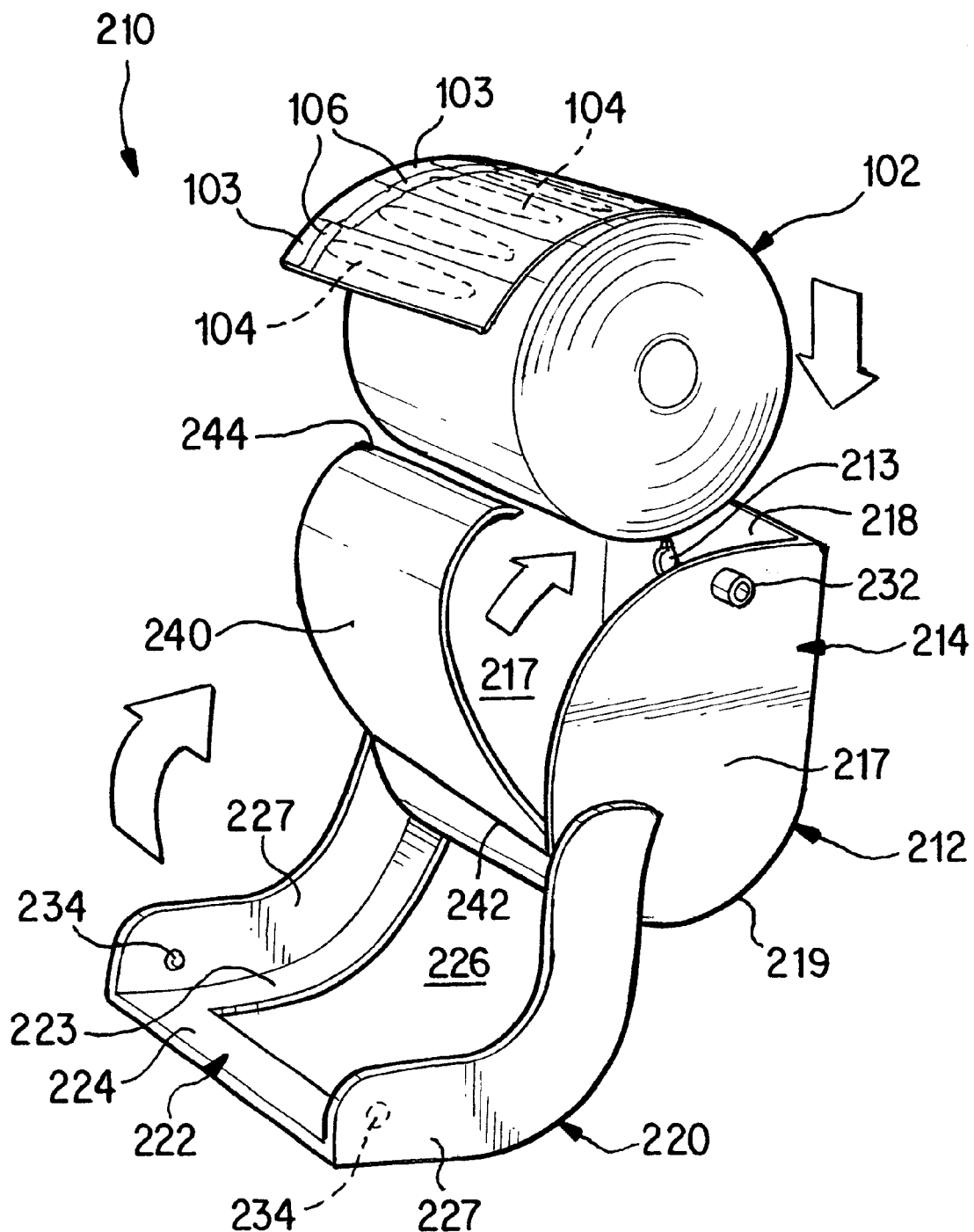
FIG. 4 is a perspective view of another embodiment of the dispenser according to the present invention in an open position.

FIGS. 4–7 illustrate a bandage dispenser 210 that can be secured to a vertical surface, such as a wall, or positioned on a horizontal surface during use. The dispenser 210 includes a housing 212 that has a bucket 214 formed by first and second opposing sidewall panels 217 and a back panel 218. The bucket 214 receives and houses the roll 102 of bandages 104 as illustrated in FIG. 4. The sidewall panels 217 can each include a protrusion for engaging side opening of an axle about which the roll 102 is reeled for supporting the roll 102 within the housing 212. Alternatively, the dispenser 210 could include an elongated rod or hollow tube that axially supports the roll 102 in any known manner and engages the sidewalls 217 in order to support the roll 102 within the housing 212. The back panel 218 has a bottom, curved section 219 that follows the general contour of the roll 102 of bandages 104. In an embodiment, the roll 102 is not supported within the housing 212. Instead, it merely rests inside of bucket 214 on the inner surface of section 219 and rotates relative to the section as the backing 103 is pulled at a dispensing end of the housing 212. The back panel 218 can also include openings 213 that receive fasteners or hooks for securing the dispenser 210 to a vertical surface. Any known manner of mounting a dispenser on a vertical surface can be used with the present invention.

The dispenser housing 212 also includes a front cover 220 having a front panel 222 and opposing sidewall panels 227 that extend along the outer surfaces of the sidewall panels 217 as seen in FIG. 4. The front panel 222 also has a centrally located opening (window) 226 through which the bandages 104 are removed from the roll 102. As illustrated in FIGS. 4 and 6, side sections 223, a front section 224 and a rear section 225 of the front panel 222 surround and define the window 226. In a preferred embodiment, the bandages 104 can be removed from backing sheet 103 through window 226 by grabbing a pull-tab 106 and applied to the patient using only a single hand as discussed below.

As shown in FIG. 6, the cover 220 is secured to the housing 212 at two points along each sidewall panel 217. For clarity of the explanation, only the connections on one of the sidewall panels 217 are illustrated. The connections on the other sidewall panel 217 are identical so no additional discussion is warranted. At a first connection point 230, the sidewall panel 217 includes a pivoting connector 232 that cooperates with a pivot member 234 on the inner surface of the sidewall panel 227 so that the cover 220 can be easily and quickly connected and disconnected from the bucket 214. In the embodiment illustrated in FIG. 4, the pivoting connector 232 includes a recess and the pivot member 234 includes a protrusion that is pivotally received within the recess 232 so that it and the cover 220 can rotate relative to the pivoting connector 232. Alternatively, the pivoting connector 232 could include the protrusion and the pivot member 234 could include the recess in which the pivoting connector rotates. Other known pivotable connections can also be used to pivotally connect the front cover 220 to the bucket 214.

Figure 7:
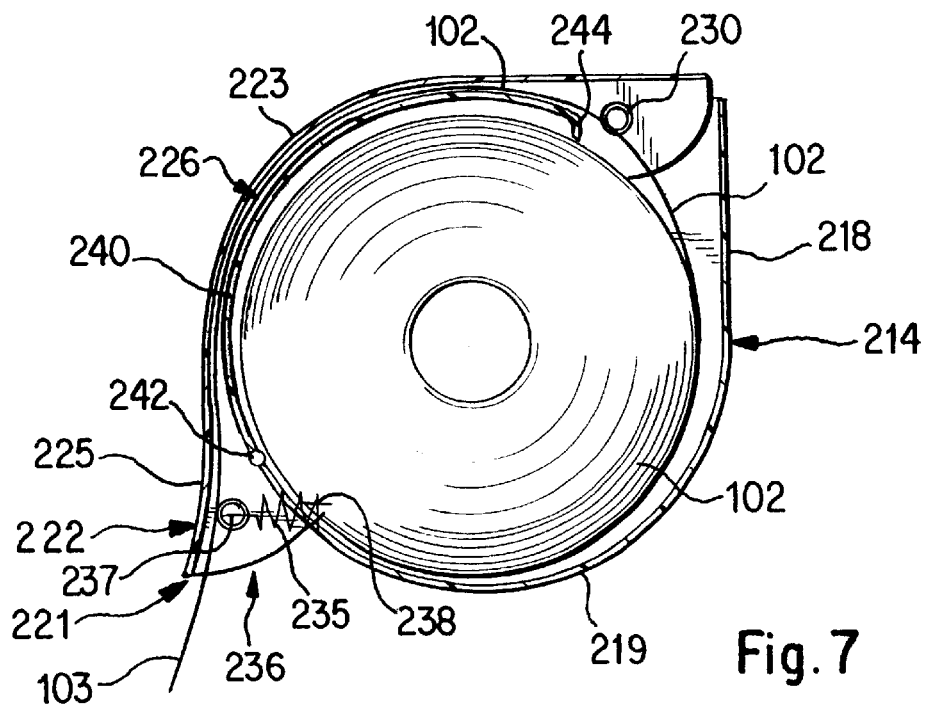
FIG. 7 is a cross section of the dispenser shown in FIG. 4 taken along the lines 7—7 in FIG. 6.

At a second connection point 236 (FIG. 6), the cover 220 is moveably connected to the sidewall panel 217 by a spring 235 that is not extended when the dispenser 210 is at rest. However, when the pulling of the roll 102 or the removal of a bandage 104 moves the cover 220, the spring 235 experiences tension and its natural bias counters the movement as discussed below. The movement of the cover 220 relative to the bucket 214 typically includes a rotary component and a linear component. FIGS. 6 and 7 illustrate that the spring 235 is a coil spring. However, any known type of spring could be used in place of the coil spring. The spring 235 has a first end 237 secured to the sidewall panel 217 and a second end 238 attached to the cover 220. In one embodiment, the connection point of the spring 235 to the cover 220 can be in/on the sidewall panel 227 proximate the front panel 222. Alternatively, in another embodiment, the connection of the spring 235 to the front cover 220 can be in/on the front panel 222. The spring 235 can be connected to sidewall panels 217, 227 or the front panel 222 using any known spring connection members. For example, the ends of the spring 235 can be positioned within an opening in the panels 217, 222, 227 or they can be positioned and secured around a member extending from an external surface of sidewall panel 217 and an interior surface of panel 222 or 227.

In addition to the spring 235, a member extending within a groove formed in the sidewall panel 217 could also connect the cover 220 to the bucket 214. The member is slidable within the sidewall groove so that the cover 220 can move relative to the bucket 214 as discussed below.

FIGS. 4 and 5 also illustrate a bandage support plate 240 that is positioned beneath the front cover 220 during the operation of the dispenser. The support plate 240 is larger than the window 226. As shown in FIGS. 4 and 5, the support plate 240 extends across the width of the dispenser 200 from one sidewall panel 217 to the other sidewall panel 217. As a result, the support plate 240 is coextensive with the window 226 and the sections 223–225 of the front cover 220 that surround and define the window 226. The support plate 240 is a hinged or cantilevered member pivotally connected to the bucket 214 only along its lower end 242. As a result, the support plate 240 can rotate (pivot) at its lower end 242 toward the bucket 214 or away from the bucket 214. As used herein, the term "rotate" includes motion of an object along an arcuate path; this motion does not need to sweep out a complete revolution. For example, as shown in the figures, the support plate 240 can be rotated (pivoted) away from the bucket 214 when the cover 220 is pivoted down and away from the top of the bucket 214 to allow the insertion of the roll 102 of bandages 104. Similarly, the support plate 240 can be rotated (pivoted) toward the interior of the bucket 214 when the cover 220 is pivoted to a closed position. The support plate 240 pinches or otherwise holds the backing sheet 103 against the inner surfaces of at least sections 223 of the cover 220 so that the backing sheet 103 will not pull through the window 226 as a bandage 104 is removed from a roll 102.

As shown in FIG. 7, when the cover 220 is in a closed position, an upper end 244 of the plate 240 is spaced from the back panel 218 by distance that is greater than the thickness of the bandage 104 and the backing sheet 103 so that the bandages 104 can be presented in the window 226 on top of the support plate 240. Also, the support plate 240 will not deflect in response to pressure applied to its upper surface when a person is removing one or more bandages 104 from the backing sheet 103. This can be accomplished by forming the support plate 240 of a rigid plastic that will not deflect into the bucket 214. Additionally, in an embodiment, the inner surface of each sidewall panel 217 can include a protruding member (not shown) that extends into the interior of the bucket 214 and limits how far the support plate 240 can pivot into the interior of the bucket 214. When pivoted to the closed position, the front panel 220, the bucket 214 and the support plate 240 enclose the loaded roll 102 of bandages 104 within the dispenser 210 as shown in FIGS. 5–7.

During the operation of the dispenser 210, the bandages 104 are delivered to the window 226 by a person pulling on a portion of the backing sheet 103 that extends away from the discharge end 211 (opposite the end where the roll 102 extends between the plate 240 and the back panel 218) of the dispenser 210. As the bandages 104 leave roll 102, pass over support plate 240 and enter the window 226, a person grasping a pull-tab 106 on the bandage cover sheet 105 can individually remove the bandages 104 from backing sheet 103. As discussed above, a line of perforations 107 that permits easy separation of adjacent bandages 104 can separate adjacent cover sheets 105. After the bandage(s) 104 have been removed from the backing sheet 103, they can be applied to a patient. In a preferred embodiment, these removal and application steps are carried out using only a single hand. As seen in FIG. 6, multiple bandages 104 are exposed in the window 226. As a result, multiple bandages 104 can be simultaneously separated from the backing sheet 103 and applied in the same manner. The end of the backing sheet 103 extending from discharge end 211 can be torn off at a random position or along a line of perforations and thrown away.

As discussed above, the spring 235 holds the cover 220 in contact with the bucket 214. The pressure applied to the cover 220 by the spring 235 and the positioning of the first connection point 230 causes the cover 220 to pinch against at least the portion of the backing sheet 103 that is coextensive with the window 226. The positioning of the pull-tabs 106 at a point between the longitudinal edges of the backing sheet 103 that causes the pull-tabs 106 to be accessible through the window 226 allows for the bandages 104 to be removed from the backing sheet 103 as the sections 223 of the cover 220 securely hold the backing sheet 103 in place and prevent movement of the backing sheet 103 relative to the sidewall panels 217 as the bandages 104 are removed. The sections 223 pinch the exposed backing sheet 103 on either side of the cover layer 105 against the support plate 240 as the support plate 240 resists deflection into the interior of the bucket 214. The lower portion 225 of the cover 220 can also pinch the backing sheet 103 against a front portion of the bucket 214 at a position below the support plate 240 and the window 226.

As mentioned above, in order to advance the backing sheet 103 and bandages 104 into and through the window 226, a user must pull the portion of the roll 102 extending from discharge end 221. This pulling of the roll 102 causes the lower, discharge end 221 of the cover 220 to pivot upward and move outward against the bias of the spring 235. As a result, the spring 235 is extended and the cover 220 moves away from the bucket 214. This releases the pressure (pinching) of the cover 220 and the support plate 240 on the backing sheet 102, allows the roll 102 to freely rotate within the bucket 214 and permits the backing sheet 103 to slide along an inner surface of the cover 220 and the support plate 240 relative to the window 226. This motion of the backing sheet 103 advances additional bandages 104 into the window 226 for removal. The backing sheet 103 can be pulled until a first bandage 104 is located at the portion of the window 226 closest to the discharge end 221.

Figure 8A:
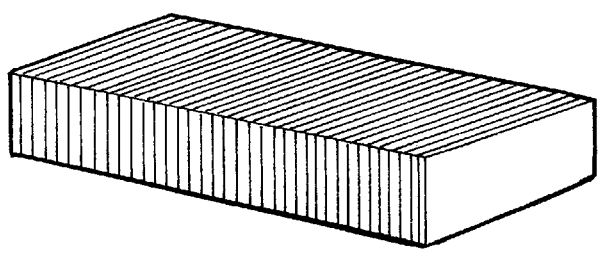
FIG. 8a is a perspective view of a bulk quantity of adhesive-backed articles, such as wrapped adhesive bandages, according to the present invention.
Figure 8B:
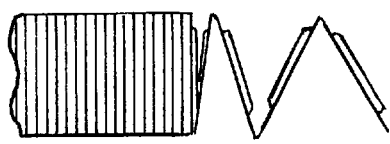
FIG. 8b is a partial side view illustrating a fan-folded bulk quantity of adhesive bandages.
Figure 8C:
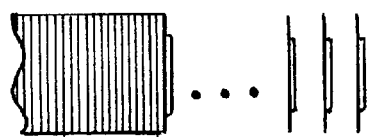
FIG. 8c is a partial side view illustrating a stacked bulk quantity of individual wrapped adhesive bandages.

FIGS. 8a–8c, illustrate examples of a bulk quantity of adhesive-backed articles 100 according to the present invention. As mentioned above, wrapped adhesive bandages (especially, but not necessarily, those disclosed in Schroeder) are discussed herein by way of example. FIG. 8a illustrates a cuboid bulk quantity 1000 of, for example, adhesive bandages. The arrangement of each wrapped adhesive bandage is discussed elsewhere herein or in the U.S. patents mentioned above, so a detailed explanation of the arrangement of each wrapped bandage is omitted here.

As seen in FIG. 8b, bulk quantity 1000 of bandages may be arranged as a continuous fan-folded length of backing 1002, wherein one or more adhesive bandages 1004 are provided on each respective fanfold segment 1006. Alternatively, the bulk quantity 1000 of bandages may be a stacked quantity of individual packets 1008 on which one or more adhesive bandages 1004a are provided.

FIG. 9 is a cross-sectional view of an adhesive bandage dispenser 1010 for a bulk quantity 1000 of adhesive bandages or the like. Dispenser 1010 is generally a rectangular box 1012 having a dispensing slot 1014 defined therein. Dispensing slot 1014 may be located anywhere on an exterior of box 1012 in alignment with either a lengthwise edge of the adhesive bandages or a widthwise edge of the adhesive bandages (see, for example, FIGS. 10*a* and 10*b*, respectively). Preferably, one side of the box 1012 is selective removably or otherwise openable (such as pivotably about a hinge, such as at 1016 in FIG. 9) so that the bulk quantity 1000 of bandages can be loaded into box 1012.

Dispenser 1010 preferably includes an urging mechanism to urge the bulk quantity 1000 towards dispensing slot 1014 so that respective adhesive bandages can be readily grasped for removal through dispensing slot 1014. The urging mechanism can be of any suitable and known form. For example, an urging member 1020 may be resiliently biased by a spring 1022 or the like towards dispensing slot 1014. The bias force provided should preferably not be overly strong, otherwise the fanfold segments are pressed together very tightly, making it difficult to pull respective wrapped adhesive bandages through dispensing slot 1014. When loading dispenser 1010, a user may, for example, manually compress urging member 1020 with, for example, a finger, while bulk quantity 1000 is loaded into box 1012. The user would thereafter release urging member 1020 so that it urges bulk quantity 1000 towards dispensing slot 1014.

Dispenser 1010 is equally applicable to a stack of individual adhesive bandage packets 1008, such as that illustrated in FIG. 8*c*. In this case, individual packets 1008 are pulled out of box 1012 through dispensing slot 1014. Again, the bias force provided by spring 1022 should not be too strong. Otherwise, the individual packets 1008 become jammed together tightly and are difficult to remove through dispensing slot 1014.

In order facilitate access through dispensing slot 1014, a thumb notch 1018 may be provided. See, also, elements 1018*a* and 1018*b* in FIGS. 10*a* and 10*b*.

Generally, the dispensing slot 1014 is provided in alignment with a lengthwise edge of a respective adhesive bandage (such as dispensing slot 1014*a* provided in dispenser 1000*a* in FIG. 10*a*). Alternatively, the dispensing slot can be provided in alignment with a widthwise edge of a respective adhesive bandage (such as dispensing slot 1014*b* provided in dispenser 1000*b* in FIG. 10*b*).

A width $Y_1$, $Y_2$ of dispensers 1000*a*, 1000*b* may vary between generally corresponding with a single adhesive bandage to corresponding with two or more adhesive bandages. For example, $Y_2$ can be made to equal, for example, $2*Y_1$. If a fan-folded bulk quantity 1000 is used, the number of bandages provided on each fanfold segment should be limited so that the fanfold segments can be easily pulled from the dispenser as they unfurl.

FIG. 11 illustrates another embodiment of a dispenser according to the present invention. Dispenser 1100 is generally constructed to receive a stacked bulk quantity of individual adhesive bandage packets 1008, similar to that illustrated in FIG. 8*c*. Dispenser 1100 includes a main body 1102 and a cover 1104. Cover 1104 may be attached to main body 1102 by any known method, such as (without limitation) being snap-fit thereon, or being hingedly attached (using, for example, a hinge 1106).

Main body 1102 generally defines a holding chamber for receiving bulk quantity 1000 that has at least one open side (covered by cover 1104). For example, main body 1102 may include two side walls (one of which is seen partly in phantom in FIG. 11, the other facing away from and to the right, with respect to the reader), a rear wall (facing away and to the left, with respect to the reader), and an endwall (facing toward the bottom of the page, with respect to the reader).

Cover 1104 includes a window 1108 formed so as to cover an end of main body 1102 opposite its endwall. The side of window 1108 generally corresponds to the length of an adhesive bandage 1110 and to the width of the total number of adhesive bandages in each packet 1008 (here, three adhesive bandages are provided in each packet 1008 by way of example).

One can either remove an entire packet 1008 (including, for example, three adhesive bandages as illustrated in FIG. 11) by way of window 1108, or one can remove individual adhesive bandages 1110 from an underlying backing sheet of the packet 1008 so that the adhesive bandage 1110 is ready for one-handed application in accordance with, for example, the manner described in the Frank and Schroeder patents. If respective adhesive bandages 1110 are removed individually, the underlying backing sheet that is left over may be removed by any known method to expose an underlying packet 1008. It is particularly desirable to constrain a given packet 1008 when an individual adhesive bandage 1110 is sought, so that the adhesive bandage 1110 can be separated from the underlying backing (not shown here) without pulling or tending to pull the entire packet 1008 through window 1108.

Main body 1102 and cover 1104 may be made out of any suitable material, especially a material that can be easily sterilized.

Figure 12A:
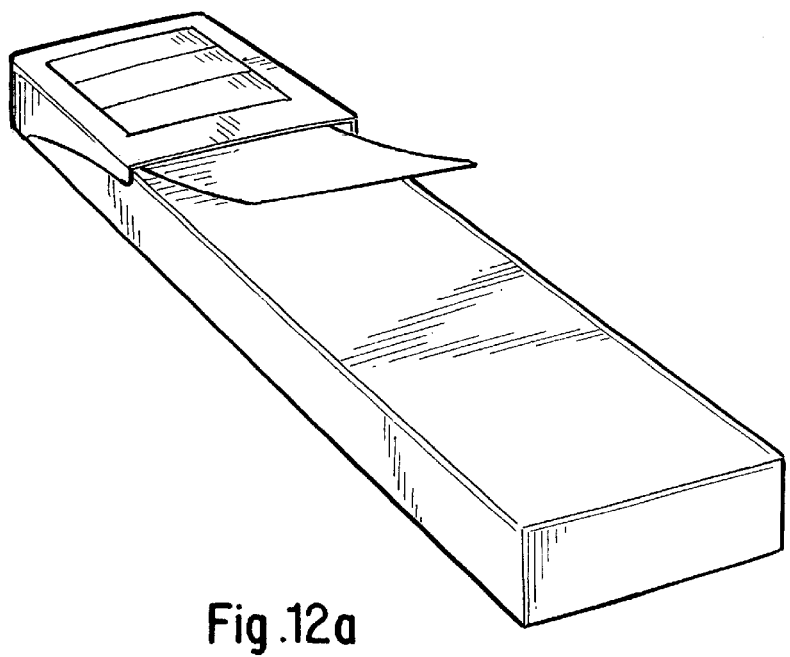
FIGS. 12a and 12b are perspective views of respective variations of an adhesive bandage dispenser according to another embodiment of the present invention.
Figure 12B:
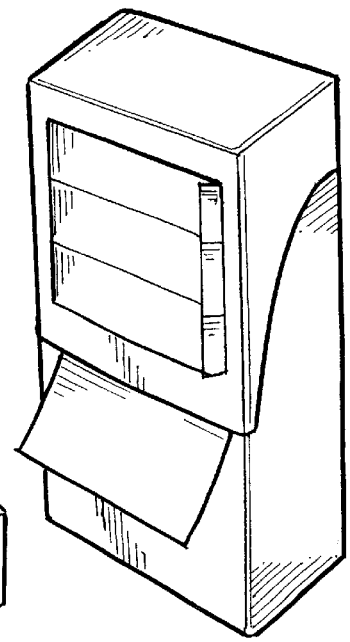

FIGS. 12*a* and 12*b* illustrate variants of another dispenser embodiment according to the present invention. Generally, dispensers 1200*a* and 1200*b* receive a fan-folded bulk quantity 1000 (such as that illustrated in FIG. 8*b*).

Dispenser 1200*a* comprises a main body 1202*a* and a cover 1204*a* that is selectively engageable with main body 1202*a* (for example, by a snap-fit or by a hinged coupling or by any other suitable mechanism). Generally main body 1202*a* is a rectangular box having an open end (shielded from view in this illustration by cover 1204*a*) through which main body 1202*a* is loaded with bulk quantity 1000 and through which fanfold segments 1006 are fed. More particularly, when cover 1204*a* is in place, fanfold segments are fed there under so that a free end 1208*a* is accessible. Cover 1204*a* has a window 1210*a* through which individual adhesive bandages 1004 are accessible. As adhesive bandages 1004 are removed through window 1210*a*, the underlying backing is advanced (for example, by manually pulling on free end 1208*a*) so that more adhesive bandages 1004 are made accessible through window 1210*a*. It will therefore be appreciated that the tolerance between main body 1202*a* and cover 1204*a* should be sufficient to permit free end 1208*a* to be freely pulled under cover 1204*a* as desired.

It will be appreciated that bulk quantity 1000 is folded along a lengthwise edge of adhesive bandages 1004, but there is no reason why it cannot be folded along a widthwise edge of adhesive bandages 1004.

Dispenser 1200*b* is substantially identical to dispenser 1200*a*. However, it will be appreciated that dispenser 1200*b* is shorter and thicker than dispenser 1200*a*. By varying both dimensions in this manner, the same quantity of adhesive bandages can be held in different amounts of volumetric space, depending on a user's needs.

Figure 13:
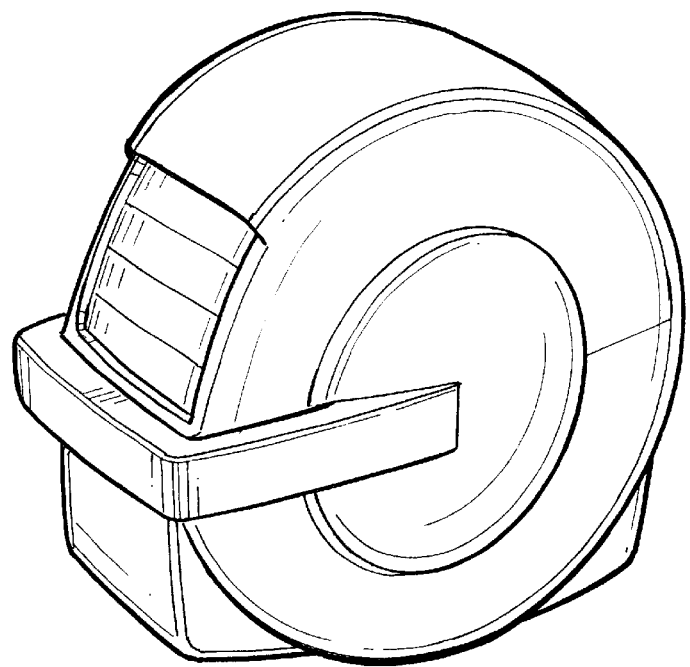
FIG. 13 is a perspective view of an adhesive bandage dispenser according to another embodiment of the present invention.

FIG. 13 is a perspective view of another dispenser embodiment according to the present invention. Here, however, a rolled bulk quantity 1000*a* of bandages is provided, from which a plurality of individual adhesive bandages are supplied.

Figure 14A:
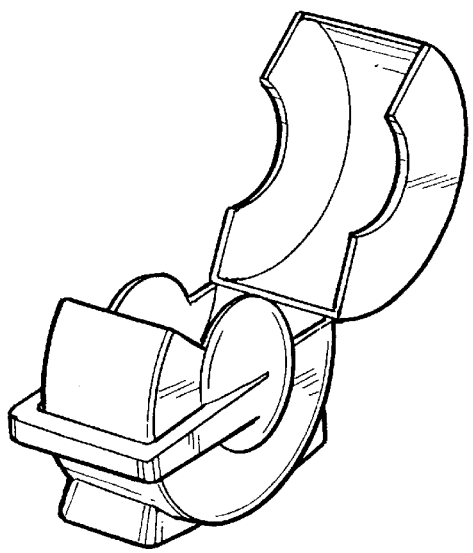
FIGS. 14a–14d illustrate loading the adhesive bandage dispenser shown in FIG. 13 with a bulk quantity of adhesive bandages provided on a rolled continuous web of backing.
Figure 14B:
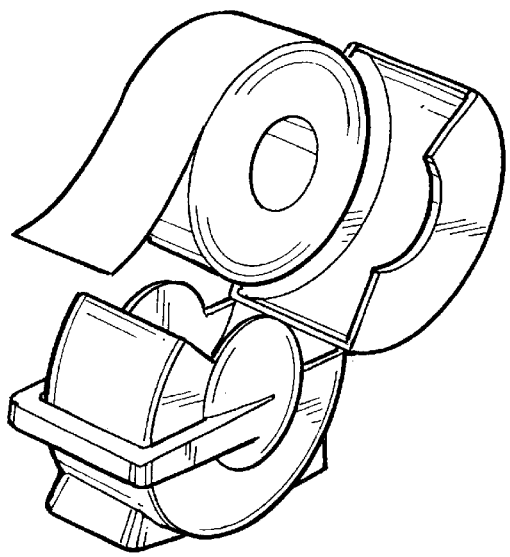

As seen in FIG. 14a, dispenser 1300 includes a main portion 1302 and a cover 1304. Main portion 1302 and cover 1304 cooperate to define a holding portion 1303 for rolled bulk quantity 1000a. Main portion 1302 and cover 1304 may be engaged in any known manner. For example and without limitation, a folding hinge 1306 is shown in FIGS. 14a–14d for joining main portion 1302 and cover 1304. Folding hinge 1306 can be formed, for example, in the process of molding main portion 1302 and cover 1304.

Main portion 1302 includes a retainer 1308 that defines a retainer groove 1310 between retainer 1308 and an outer surface of main portion 1302.

Figure 14C:
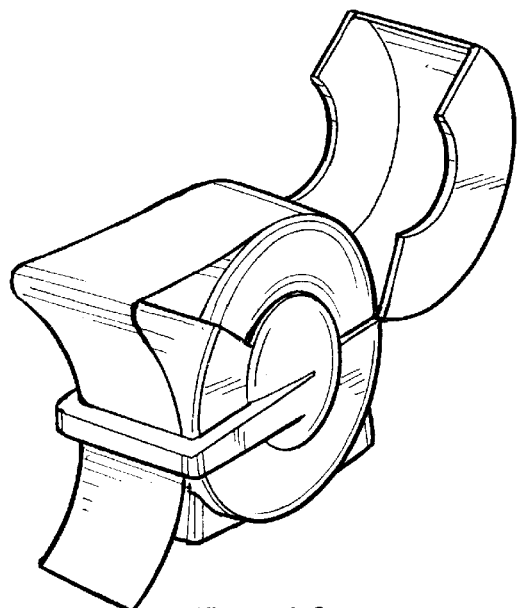
Figure 14D:
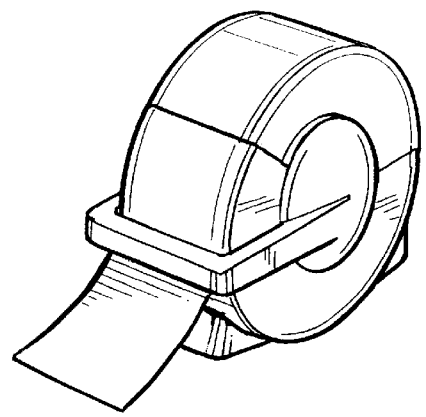

Rolled bulk quantity 1000a is placed in holding portion 1303, and a free end 1312 is threaded into retainer groove 1310 (as seen in FIG. 14c). Rolled bulk quantity 1000a is arranged so that respective adhesive bandages provided thereon face outwardly. As a result, when cover 1304 is closed, a window 1314 allows respective adhesive bandages to be removed from the underlying backing. As adhesive bandages are removed, the rolled bulk quantity 1000a can be advanced by, for example, manually pulling on free end 1312 until more adhesive bandages are visible in window 1314. The scrap backing extending from retainer groove 1310 can be periodically torn off or otherwise fed to a scrap storage well.

Figure 15A:
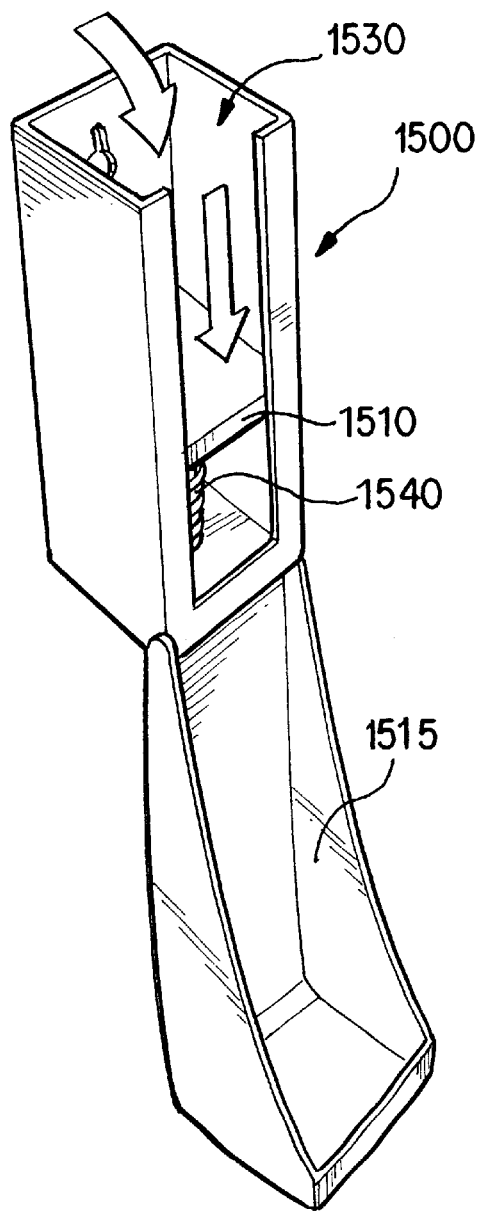
FIGS. 15a–15e illustrate additional embodiments of the dispenser according to the present invention.
Figure 15B:
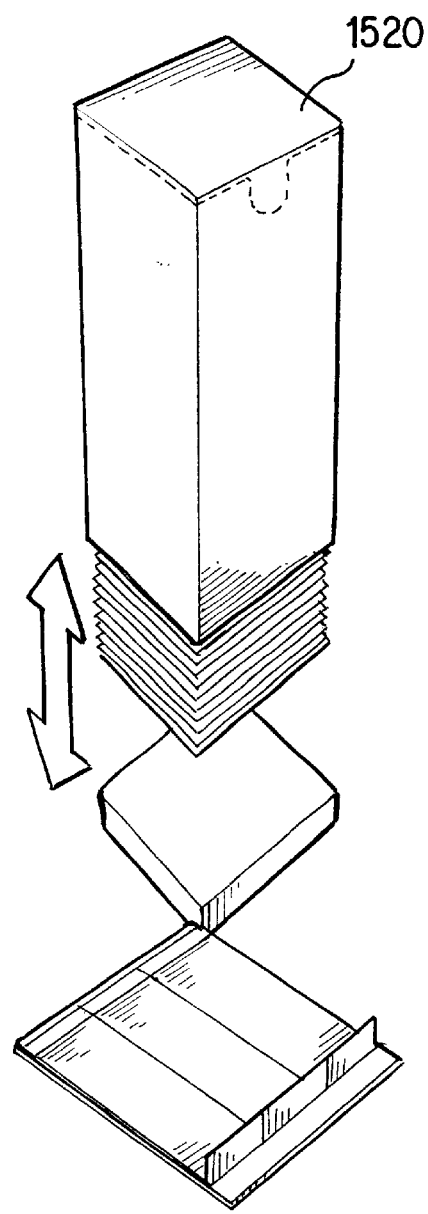

FIGS. 15a–15b illustrate alternative embodiments of the dispensers. The dispenser 1500 of FIG. 15a includes a biased plate 1510 and pivoted cover 1515 that is closed when a box of bulk bandages 1520 is positioned in a reservoir 1530 in the dispenser 1500. A spring 1540 positioned below the plate 1510 forces the uppermost bandage package to the top of the dispenser 1500 so it can be easily removed through the top of the dispenser 1500 or a front window.

Figure 15D:
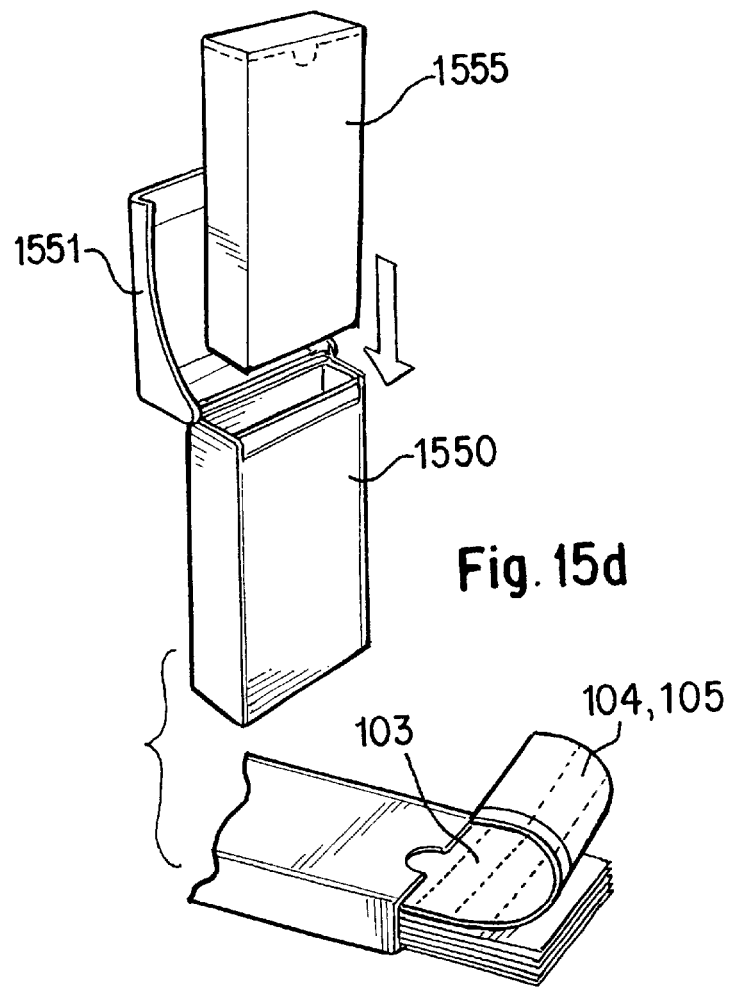
Figure 15E:
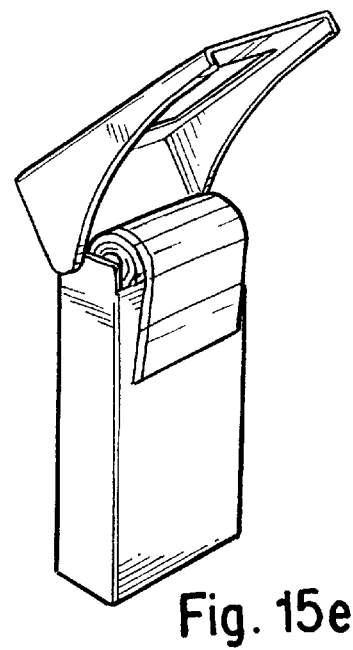
Figure 15C:
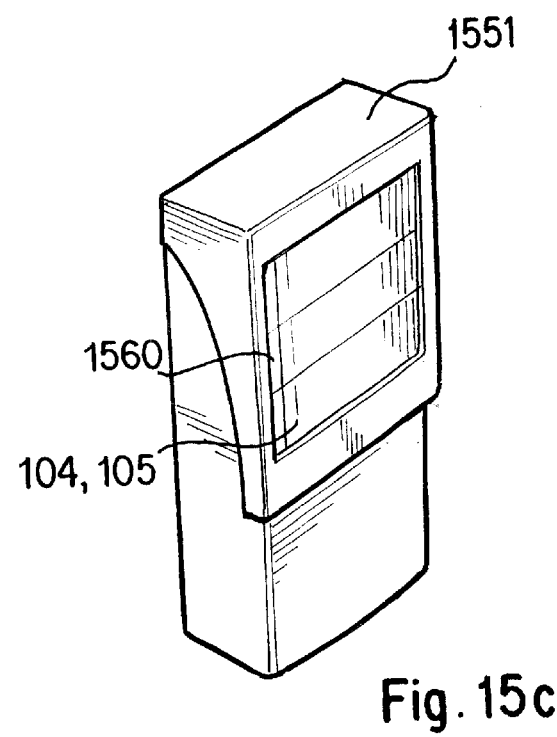

The dispenser 1550 in FIGS. 15c–15e has a hinged cover 1551 and an open reservoir that receives a box 1555 of bulk bandages 104 that are rolled or otherwise folded in the box 1555. The bandages 104 and backing sheet 103 are pulled past a window 1560 in the cover 1551 and removed from the backing sheet 103 through the window 1560 as discussed above.

Numerous characteristics, advantages and embodiments of the invention have been described in detail in the foregoing description with reference to the accompanying drawings. However, the disclosure is illustrative only and the invention is not limited to the illustrated embodiments. Various changes and modifications may be effected therein by one skilled in the art without departing from the scope or spirit of the invention.

We claim:

1. A dispenser for adhesive-backed articles carried on a backing sheet, said dispenser comprising:
   a housing including a bucket portion for receiving and containing the adhesive-backed articles to be dispensed and a cover connected to said bucket portion, said cover including a window through which the adhesive-backed articles can be removed from the backing sheet; and
   a support member secured within said housing such that said support member contacts an interior surface of said housing when said window is free of the backing sheet and is spaced from said interior surface when a backing sheet is coextensive with said window, said support member cooperates with said interior surface of said housing to prevent a longitudinal side edge of the backing sheet from entering said window as one of the adhesive-backed articles is removed from the backing sheet.

2. The dispenser of claim 1 wherein said support member is pivotally connected to said housing.

3. The dispenser of claim 2 wherein said interior surface of said housing includes said inside surface of said cover, and said support member includes a plate biased against said inside surface of said cover.

4. The dispenser of claim 1 wherein said support member is coextensive with said window.

5. The dispenser of claim 1 wherein said cover is pivotally connected to said bucket portion of said housing.

6. The dispenser of claim 5 wherein said cover is pivotally connected to said bucket portion at a first position along a sidewall panel of said bucket and at a second position along said sidewall panel spaced from said first position such that said cover is capable of pivoting relative to the bucket portion about either said position.

7. The dispenser of claim 6 wherein a spring connects said cover to said sidewall panel at said second position.

8. The dispenser of claim 7 wherein said cover is capable of moving relative to said bucket when the backing layer is pulled at a discharge end of the housing that is proximate said second position.

9. The dispenser of claim 8 wherein said spring is secured to the bucket portion such that said spring resists movement of said cover away from said bucket portion and biases said cover toward said support member.

10. The dispenser of claim 1 wherein said cover is biased toward said support member.

11. The dispenser of claim 1 wherein said housing includes a discharge opening at a discharge end of the cover.

12. A dispenser for adhesive-backed articles positioned on an elongated backing sheet, said dispenser comprising:
   a housing including a region for receiving and storing the adhesive-backed articles, and a cover connected to the storing and receiving region, said cover having an open section through which the adhesive-backed articles can be removed without opening said cover; and
   a member capable of rotary motion, said member cooperating with a portion of said housing to secure the backing sheet between said member and said portion of said housing when a portion of said backing sheet is coextensive with said opening so that said backing sheet does not move relative to the dispenser while one of the bandages is removed from the backing sheet.

13. The dispenser of claim 12 wherein said portion of said housing is rotatable relative to said cover and said member, and wherein said backing layer can be advanced when said member and said portion of said housing are rotated.

14. The dispenser of claim 13 wherein said portion of said housing and said member are rollers.

15. The dispenser of claim 14 further including a rotatable handle, and wherein one of said rollers is driven by movement of said handle.

16. The dispenser of claim 12 wherein said portion of said housing includes an inner surface of said cover.

17. The dispenser of claim 16 wherein said cover is pivotally connected to a sidewall panel of said housing at two spaced positions such that said cover is capable of pivoting relative to the sidewall panel about either said position.

18. The dispenser of claim 17 wherein a spring connects said cover to said sidewall panel at the second position.

19. The dispenser of claim 18 wherein said cover is capable of moving relative to said sidewall panel when the backing layer is pulled at a discharge end of the housing that is proximate said second position.

20. The dispenser of claim 19 wherein said spring is secured to said sidewall panel such that said spring resists movement of said cover away from the sidewall panel and biases said cover toward said member.

21. The dispenser of claim 12 wherein said cover is biased toward said member.

22. A dispenser for adhesive-backed articles carried on a backing sheet, said dispenser comprising:

a housing including a bucket portion for receiving and containing the adhesive-backed articles to be dispensed and a cover connected to said bucket portion, said cover including a window through which the adhesive-backed articles can be removed from the backing sheet; and a support member secured within said housing such that said support member contacts a portion of said housing when said window is free of the backing sheet and is spaced from said portion of said housing when the backing sheet is coextensive with the window, and at least one of said cover and said support member being biased toward the other of said cover and support member for preventing movement of the backing sheet as one of the adhesive-backed articles is removed from the backing sheet through said window.

23. A dispenser for adhesive-backed articles carried on a backing sheet, said dispenser comprising:

a dispenser housing for containing the adhesive-backed articles positioned on the backing sheet, said dispenser housing comprising a cover including an opening through which contained adhesive-backed articles can be dispensed, said opening extending through an upper surface of said cover and being spaced from terminal ends of said cover; and a mechanism positioned within said housing and moveable between a rear portion of said housing and said opening for urging adhesive-backed articles within said dispenser housing toward said opening so that the urged adhesive-backed articles can be dispensed though said opening in said dispenser housing.

24. The dispenser of claim 23 wherein said opening is at a front portion of said housing which is opposite said rear portion.

25. A dispenser for adhesive-backed articles carried on a backing sheet, said dispenser comprising:

a dispenser housing for containing the adhesive-backed articles positioned on the backing sheet, said dispenser housing including an opening through which contained adhesive-backed articles can be dispensed; and a mechanism positioned within said housing and moveable between a rear portion of said housing and said opening for urging adhesive-backed articles within said dispenser housing toward said opening so that the urged adhesive-backed articles can be dispensed though the opening in said dispenser housing, said urging mechanism includes a support plate and a spring for biasing said support plate away from said rear portion.

26. The dispenser of claim 25 wherein said spring is positioned between said support plate and said rear portion.

27. The dispenser of claim 23 wherein said opening includes a slot within said housing.

28. The dispenser of claim 23 wherein said opening includes a window through which the adhesive-backed articles can be removed from the backing sheet using a single hand.

29. The dispenser of claim 23 wherein said housing includes a main body portion and a cover portion secured to the main body portion so that said cover portion is moveable relative to said main body portion.

30. The dispenser of claim 29 wherein said cover is pivotally secured to main body portion.

* * * * *